United States Patent [19]

Polson et al.

[11] Patent Number: 5,820,550

[45] Date of Patent: Oct. 13, 1998

[54] PULSE OXIMETER WITH IMPROVED ACCURACY AND RESPONSE TIME

[75] Inventors: Michael John Ross Polson, Chesire, Conn.; Gregory Llewelyn Morris, Spittal, United Kingdom

[73] Assignee: Novametrix Medical Systems Inc., Wallingford, Conn.

[21] Appl. No.: 413,774

[22] Filed: Mar. 16, 1995

Related U.S. Application Data

[63] Continuation of Ser. No. 910,786, Jul. 8, 1992, Pat. No. 5,398,680, which is a continuation of Ser. No. 430,612, Nov. 1, 1989, Pat. No. 5,190,038.

[51] Int. Cl.$^6$ .................................................. A61B 5/00
[52] U.S. Cl. ............................. 600/323; 600/336; 356/41
[58] Field of Search ........................... 128/633, 664–667; 356/39–41; 600/310, 314, 323, 326, 336, 473, 476, 479

[56] References Cited

U.S. PATENT DOCUMENTS

| | | |
|---|---|---|
| 3,955,096 | 5/1976 | Faulhaber . |
| 4,063,551 | 12/1977 | Sweeney . |
| 4,086,915 | 5/1978 | Kofsky et al. . |
| 4,180,327 | 12/1979 | Maeda . |
| 4,407,290 | 10/1983 | Wilber et al. . |
| 4,638,810 | 1/1987 | Ramsey, III et al. ................. 128/681 |
| 4,759,369 | 7/1988 | Taylor . |
| 4,911,167 | 3/1990 | Corenman et al. .................... 128/666 |
| 4,928,692 | 5/1990 | Goodman et al. ..................... 128/666 |
| 5,190,038 | 3/1993 | Polson et al. .......................... 128/633 |
| 5,398,680 | 3/1995 | Polson et al. .......................... 128/633 |

FOREIGN PATENT DOCUMENTS 50-128387   10/1975   Japan .

OTHER PUBLICATIONS

"Spectrophotometric monitoring of arterial oxygen saturation in the fingertip" by I. Yoshiya, et al., published by Medical Biological Engineering & Computing, Jan. 1980, 6 pages.

"An Electronic Circuit for Red/Infrared Oximeters" by Eugen Schibli et al., published by IEEE Transaction On Biomedical Engineering, vol. BME 25, No. 1., Jan., 1978, 3 pages.

"Clinical Application of Fingertip Pulse Wave Oximeter" by Suzukawa, et al., published by The Japanese Journal Anesthesiology, vol. 27, No. 6., 1978, 8 pages.

Oximet brochure for Oximet pulse oximeter model MET–1471, from Mochida, 6 pages.

"Improved Extracorporeal Reflectance Oximeter" by T.P. Grover, published in Conference Proceedings of 26th Annual Conference on Engineering in Medicine and Biology, Sept. 20–Oct. 4, 1973, 1 page.

Schematics of Biox Pulse Oximeter Models II, IIA, II and IV, from Biox Technology, Boulder, Colorado, 4 pages.

*Primary Examiner*—Jennifer Bahr
*Assistant Examiner*—Bryan K. Yarnell
*Attorney, Agent, or Firm*—Hopgood, Calimafde, Kali & Judlowe, LLP

[57] ABSTRACT

An improved pulse oximeter apparatus and method for the measurement of oxygen saturation in the blood, which is faster and more accurate than conventional pulse oximeters. Improved speed and accuracy is attained by elimination of normalization and feedback circuitry and the use of analog to digital converting devices having a wide dynamic range along with a sophisticated computer analysis. The instant invention eliminates inaccuricies resulting from channel matching errors, and detects and eliminates aberrant input data.

14 Claims, 9 Drawing Sheets

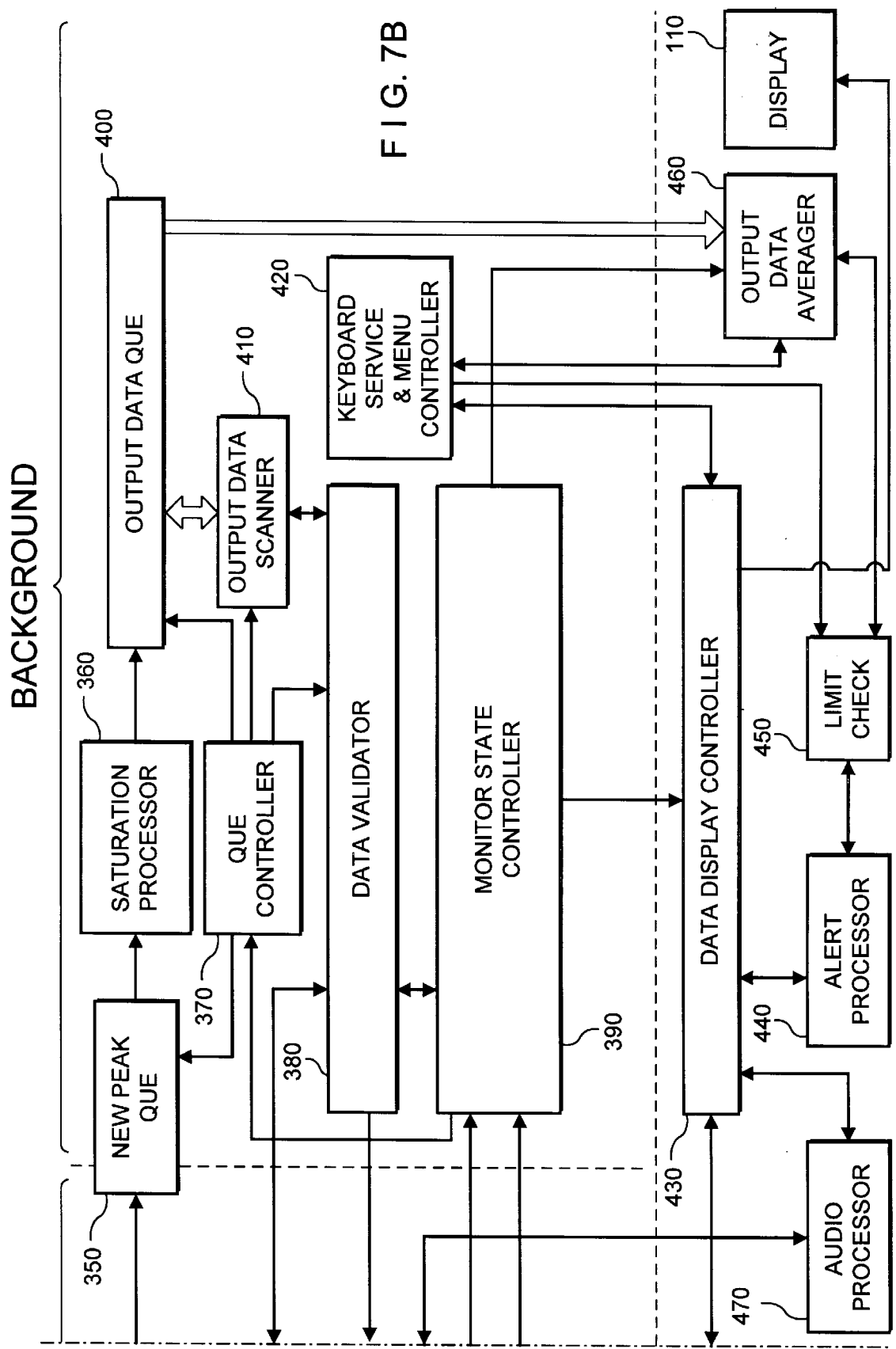

| 1 | TAG NEW OUTPUT DATA --- TRASHED. |

| 2 | INITIALIZE SCANNER PARAMETERS:
CLIP LEVEL = -1500
THRESH = - 200
TIME = 8 sec. |

| 3 | SET THE SCAN LIMIT TIME TO THE CURRENT TIME [ $t_{scan} = t_{now}$ ] |

| 4 | INDICATE ARTIFACT PRESENT, TO MONITOR STATE CONTROLLER. |

| 5 | SET SCANNER PARAMETERS BASED ON $PK_{min}$ OF NEW DATA STRUCTURE:

CLIP LEVEL = $2PK_{min}$

THRESHOLD = $PK_{min}/2$ |

| 6 | SET SCANNER TIME PARAMETER TO THE SMALLER OF: 8 seconds OR $T_{now} - t_{scan}$. THEN PERFORM A SCAN OF THE OUTPUT QUE. COPY THE RETURN PARAMETERS:
A = CLIPPED %

B = CONFIDENCE OF $PERIOD_{OK}$

C = CONFIDENCE OF $MEAN_{OK}$

D = CONFIDENSE OF $PERIOD_{CLIPPED}$

E = CONFIDENCE OF $MEAN_{CLIPPED}$ |

| 7 | UPDATE SCANNER PARAMETERS:

CLIP LEVEL = $2[MEAN_{CLIPPED}]$

THRESHOLD = $[MEAN_{CLIPPED}]/2$ |

| 8 | UPDATE SCANNER PARAMETERS:

CLIP LEVEL = $2[MEAN_{OK}]$

THRESHOLD = $[MEAN_{OK}]/2$ |

| 9 | INDICATE ARTIFACT CLEAR, TO MONITOR STATE CONTROLLER. |

| 10 | SET THE SCAN LIMIT TIME TO $t_{scan} = t_{now} - 1\,second$ |

| ?1 | IS A NEW DATA STRUCTURE PRESENT IN THE OUTPUT QUE ? |

FIG. 9

PULSE OXIMETER WITH IMPROVED ACCURACY AND RESPONSE TIME

This is a Continuation of copending application Ser. No. 07/910,786, now U.S. Pat. No. 5,398,680; which is a Continuation of application Ser. No. 07/430,612 filed Nov. 1, 1989, now U.S. Pat. No. 5,190,038.

FIELD OF THE INVENTION

The instant invention relates to apparatus for the non-invasive measurement of oxygen saturation in the arterial blood of a living person and, more particularly, to a pulse oximeter which measures oxygen saturation in the blood, faster and more accurately than conventional pulse oximeters, while at the same time providing effective discrimination against motion artifacts, and/or other aberrations in the input data.

BACKGROUND OF THE INVENTION

Pulse oximeters are well known devices used to measure the oxygen saturation of arterial blood where oxygen saturation is defined as the ratio of the total oxygen carrying capacity of arterial blood, to its actual oxygen content when measured. Known pulse oximeters calculate oxygen saturation by measuring the ratio of oxygenated hemoglobin molecules in the blood to the total number of hemoglobin molecules which are present in the same blood sample.

It is well-known that non-oxygenated hemoglobin molecules absorb more red light than oxygenated hemoglobin, and that absorption of infrared light is not affected by the presence of oxygen in the hemoglobin molecules. For this reason, all known pulse oximeters commence the oxygen saturation measurement process by directing both a visible red (VR) and an infrared (IR) light source through a blood carrying tissue sample, and thereafter known pulse oximeters detect and process the signal received after passage through the tissue sample.

More particularly, one of the earlier known techniques to measure oxygen saturation is described in a Japanese patent application to Takuo Aoyagi, which application was laid upon for publication on Oct. 9, 1973, in Laid Open Japanese Patent Publication Number SHO 50/1975-128387. Aoyagi describes an oximeter which includes an incandescent broad band light source and two separate photo detection circuits, one photo detector being overlayed with an optical filter such that it is only sensitive in the red frequency range, and the second photo detector being overlayed with a second optical filter, such that it is only sensitive in the infrared frequency range. The light energy from the light source is transmitted through a blood bearing specimen such as a finger or ear lobe, and the amount of light transmitted through the specimen is detected by two separate photo detection circuits.

Each signal from each detector circuit is separable into a constant component and a pulsatile component. The constant component, or DC component, is indicative of non-pulsating blood flow in the specimen area, while the pulsatile component, or AC component, is indicative of the pulsating blood flow in the specimen area.

A first and second calculation circuit, operating on both the red and infrared signal branches, divides the AC (pulsatile) portion of the signal, by the DC (steady state) portion of the signal, in order to standardize the amplitude of the AC portion. Thereafter, a third calculation is performed wherein the standardized AC portion of the red signal is divided by the standardized portion of the infrared signal and this ratio is indicative of the oxygen saturation level.

Although Aoyagi was one of the earlier known techniques to measure the oxygen saturation level in blood, the necessity to perform three separate calculations, and perform those calculations with analog, rather than digital circuitry, resulted in a relatively inaccurate measuring technique that also had a slow response time.

A second device for measuring the oxygen saturation level of the blood is set forth in U.S. Pat. No. 4,407,290 to Wilber, issued on Oct. 4, 1983. Wilber describes a blood constituent measuring device capable of determining the concentration of certain blood constituents such as hemoglobin and oxyhemoglobin, and use of that information to determine oxygen saturation of the blood. More particularly, an AC modulated pulse train is developed, which pulse train is indicative of light transmitted through a tissue sample at both a red and infrared wavelength. Wilber specifically teaches that the received pulses are normalized by scaling both the AC and DC components of each light source signal, so that the DC (average) component from each light source is made equal to a known preset level. This normalization procedure is required in Wilber, in order to accomplish an accurate subtraction of the DC component of each signal in each channel from the total signal, so that the resultant signal is essentially only an AC component on a zero reference level. After the DC components are removed, the AC signal components are multiplexed and converted to digital form for processing in a digital processor.

Although the Wilber patent has certain advantages over the prior techniques of Aoyagi, such as digital processing, it still suffers from the disadvantage that it must normalize the received signals in order to obtain a relatively accurate measurement of oxygen saturation levels. The necessity to normalize such signals inherently delays the measurement process resulting in a relatively slow response time for the device, and also substantially increases cost due to the extra circuitry required.

A final, and more advanced, technique in the area of pulse oximeters is described in U.S. Pat. No. 4,759,369, which issued to Andrew C. Taylor on Jul. 26, 1988, which patent is assigned to the same assignee as the instant invention. The teachings of U.S. Pat. No. 4,759,369 are specifically incorporated herein by reference. The Taylor device attempts to overcome the disadvantages, such as those described in the Aoyagi and Wilber references, by providing a simplified pulse oximeter design with improved accuracy and reduced calculation time. More particularly, the Taylor patent teaches the use of first and second light sources, the first light source generating energy in a red wavelength and the second light source generating energy in an infrared wavelength. The light sources are directed through a blood carrying tissue sample and the amount of light transmitted through the tissue sample is detected by a photo detector. The signals (red and infrared) received by the photo detector, are separated into a constant (DC) component and a pulsatile, i.e. time varying (AC) component. The AC portion of the signal is divided by the total signal (AC and DC) to standardize the AC signal, and the standardized AC red signal is then divided by the standardized AC infrared signal to obtain the necessary ratio for the determination of oxygen saturation.

A specific object and feature of the Taylor invention was the necessity to scale the level of the input signals in order to insure that those input signals did not exceed the dynamic range of an analog/digital (A/D) converter included within the circuit, which analog/dialog converter functioned to convert the AC analog signals into a digital signal suitable for processing by an attendant digital computer. This scaling feature is accomplished by two separate gain control circuits which function to adjust the drive currents to the red and infrared light sources. The adjustment process effects the entire signal (AC and DC), to ensure that this signal falls within a range which can be accommodated by the A/D converter.

Although the Taylor device is superior to other prior art pulse oximeter devices, the necessity to scale input signals so that those signals can be accommodated by the range of an A/D converter reduces both the inherent accuracy and response time of the device described in the Taylor reference.

In addition to the foregoing limitations described with respect to the Aoyagi, Wilber and Taylor devices, such prior art pulse oximeters have several additional disadvantages. First, all three devices utilize the hardware portion of the circuitry to separate the DC component from the AC component for both the IR and VR channels, with the AC component being amplified separately from the DC component. As each separate amplifier does not provide exactly the same amount of gain, inaccuracies are introduced into the measurement process when the ratio of the AC component to the DC component is calculated. This "channel matching" problem then results in an inherent inaccuracy in the calculated oxygen saturation level.

Also all three prior art devices do not effectively discriminate against motion artifacts (or other aberrant input data), where a motion artifact is defined as a large false signal generated when there is inadvertent relative movement between the tissue sample and the input sensors. Failure to detect and effectively eliminate aberrant input data in such devices, can result in inaccurate information being provided to an operator of the pulse oximeter.

It is, therefore, an object of the instant invention to provide a pulse oximeter device capable of greater accuracy then the prior art device described above, along with the ability to provide an improved response time for processing incoming information and displaying an oxygen saturation level.

It is a further object of the instant invention to eliminate inaccuracies resulting from channel matching errors when calculating an oxygen saturation level.

It is a still further object of the instant invention to provide means to effectively discriminate against motion artifacts and other aberrant input data in a pulse oximeter circuit.

SUMMARY OF THE INVENTION

In accordance with a first aspect of the instant invention, first and second light sources direct light through a blood carrying tissue sample, the first light source generating light of a first wavelength and the second light source generating light of a second wavelength.

It is a feature of the invention that the light energy is detected after passage through the tissue sample and, in response thereto, an electrical signal is generated having a magnitude related to the degree of oxygen saturation in the blood, the magnitude of the electrical signal being less than a known maximum signal magnitude, and more than a known minimum signal magnitude, and having an AC and a DC component.

In accordance with a further aspect and feature of the invention, the electrical signal includes first and second portions related respectively to the first and second light sources, and each signal portion is converted into a selected digital signal by an analog to digital conversion device specifically designed to accommodate both the maximum and minimum signal amplitudes.

It is another feature of the invention that the selected digital signals produced by the analog to digital converter are processed by an attendant central processing unit which utilizes the digital signals to calculate the oxygen saturation level in the measured blood sample.

It is a further feature of the invention that the central processing unit utilizes a series of software routines to analyze the selected digital signals, and as part of that analysis separates the DC component from the AC component for each portion of the analog signal, which separation does not occur in the hardware portion of the pulse oximeter circuit.

It is a still further feature of the instant invention that the analysis performed by the central processing unit includes the ability to identify and eliminate motion artifacts and other aberrant input data.

In accordance with another aspect and feature of the invention, ambient light levels adjacent to the tissue sample are detected and an alarm is activated if the ambient light level exceeds a predetermined amount.

The foregoing and other objects and features of this invention will be more fully understood from the following description of an illustrative embodiment thereof, taken in conjunction with the accompanying drawings.

BRIEF DESCRIPTION OF THE DRAWING

In the Drawings:

FIG. 9 is a list describing each operation undertaken by the Data Validator for each state illustrated in the state diagram of FIG. 8.

DETAILED DESCRIPTION

U.S. Pat. No. 4,759,369 to Taylor (the '369 patent) describes a sophisticated pulse oximeter which has enjoyed substantial commercial success. The instant invention is an improvement over the device described in the '369 patent.

Figure 1A:
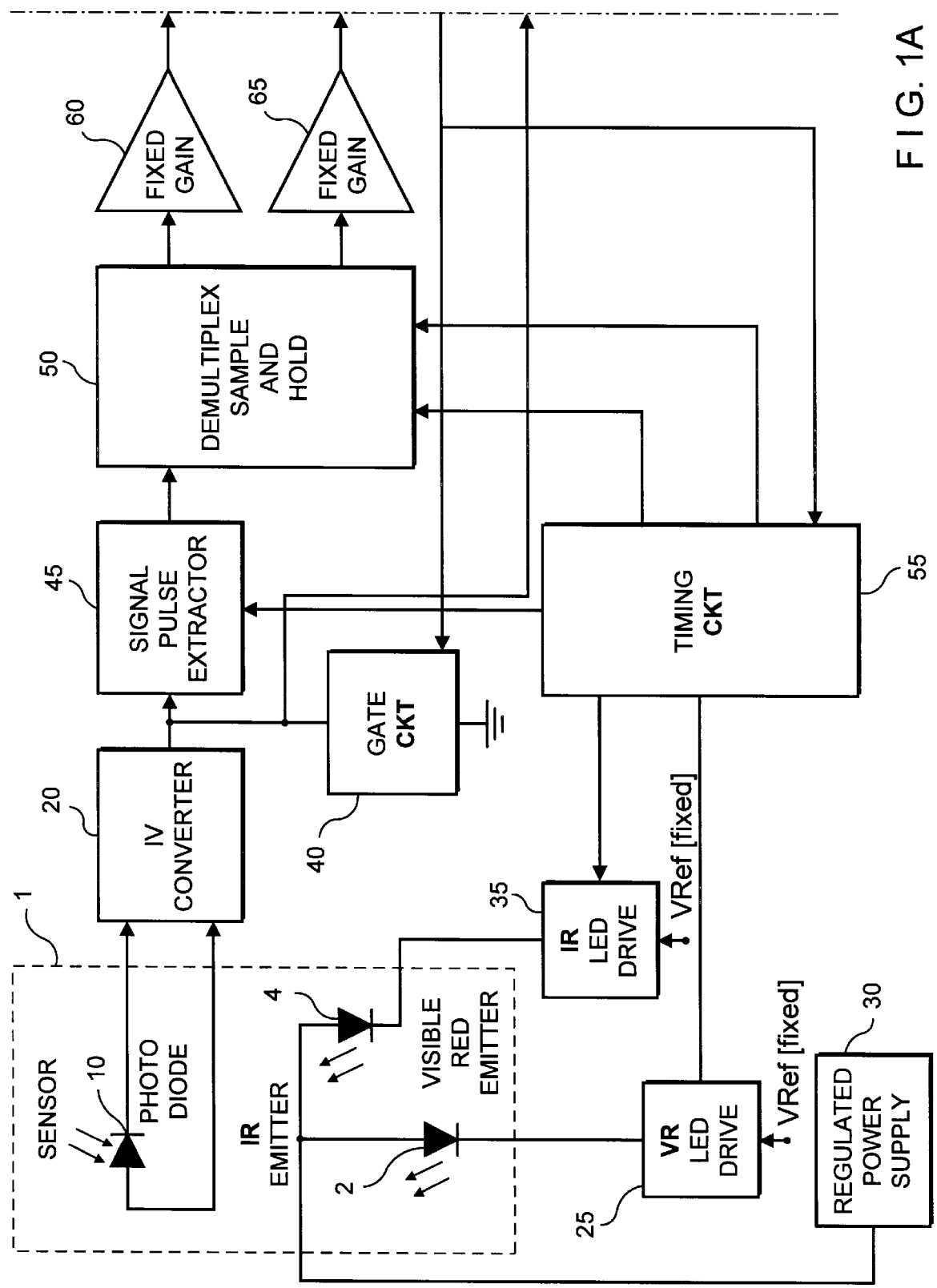
FIG. 1 illustrates, in block diagram form, the various components of a pulse oximeter in accordance with the instant invention.
Figure 1B:
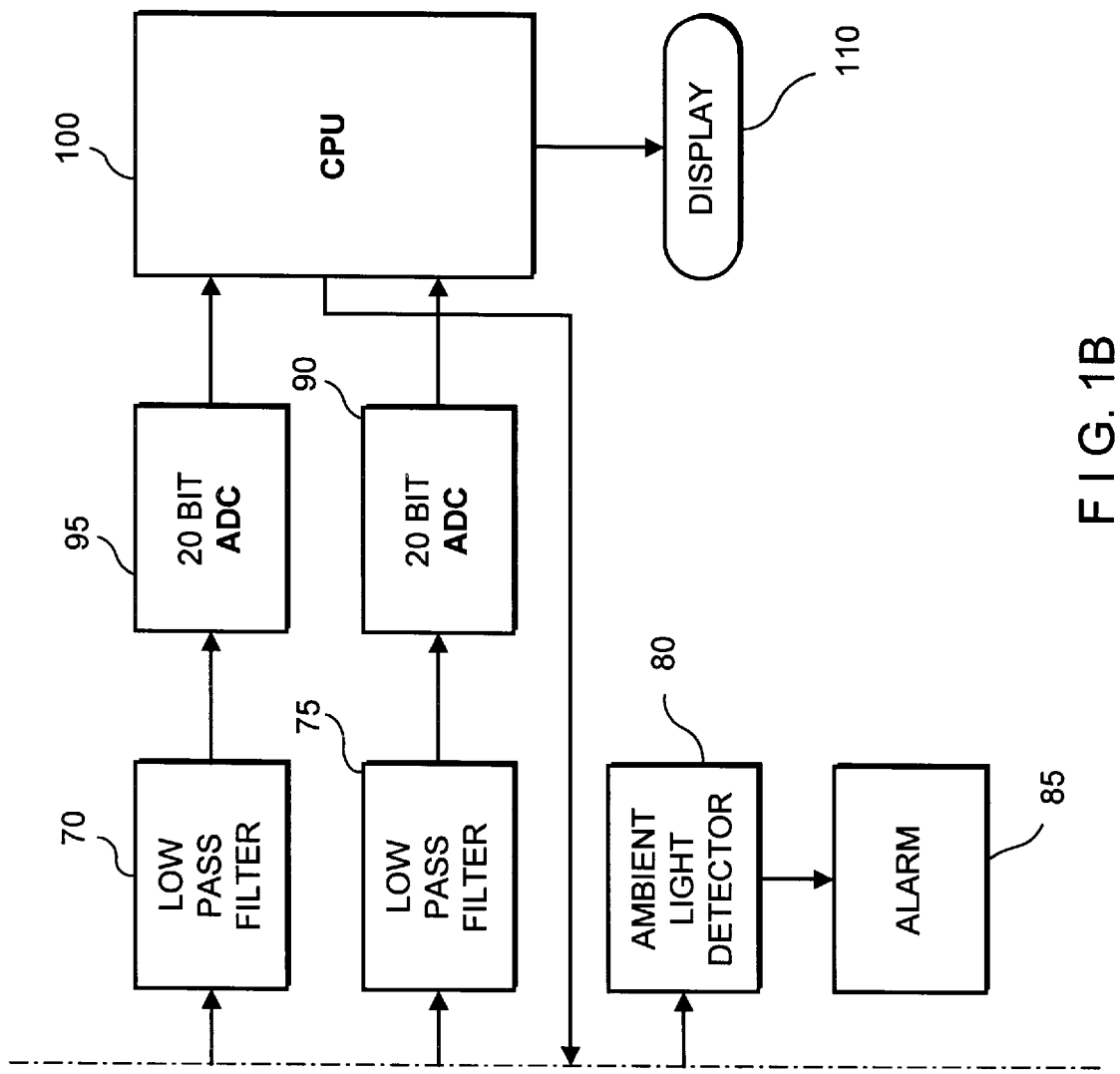

More particularly, referring to FIG. 1, oxygen saturation of the blood is determined by directing an infrared light source and a visible red light source through blood bearing tissue. The visible red emitter 2, and the infrared emitter 4, are shown within housing 1 which also includes sensor 10. The sensor can, for example, be a photo diode which functions to detect the light from the infrared and visible red emitters after the light has passed through blood bearing tissue.

The particular physical arrangement of the infrared and visible red emitters and the sensor is illustrated in FIG. 1 of the '369 patent. As discussed therein, the emitters can include, for example, a first LED emitting light at a frequency of 660 nano meters, and a second LED emitting light at a frequency of 940 nano meters. The light from each of the infrared and visible red emitters is directed through blood bearing tissue such as a finger or earlobe. Photo diode 10 is mounted on the opposite side of housing 1 having a light sensitive face orthogonal to the axis of the maximum light emission from the infrared and visible red emitters. The visible red emitter 2 and the infrared emitter 4 are driven respectively by visible red LED drive source 25 and infrared LED drive source 35.

Drive circuits 25 and 35 are controlled by timing circuit 55 which, in turn, may be controlled by commands from CPU 100. More particularly, circuit 55 selectively activates drive circuits 25 and 35 to apply selective and sequential pulse signals to the visible red emitter 2 and infrared emitter 4 respectively. Both the infrared emitter and the visible red emitter are also connected to regulated power supply 30 which applies a fixed current to the anodes of both emitters. In response to the control pulses from drive circuits 25 and 35, the emitters 2 and 4 are sequentially pulsed on and off to direct, in sequence, infrared and visible red light through the blood bearing tissue.

A specific feature of the instant invention is that drive circuits 25 and 35 are controlled by a fixed voltage reference, (VRef.), which fixed voltage is applied to emitter devices 2 and 4 in response to the control pulses from timing circuit 55. Due to the fact that the reference voltage applied by drive circuits 25 and 35 is fixed, the energy level output from emitters 2 and 4 also remains at a fixed level proportional to the fixed level of the reference voltage. Therefore, the output of photo diode 10 will vary between two known levels, a known maximum amplitude level and a known minimum amplitude level dependent upon the tissue sample under consideration and ambient light levels. This is in contrast to the device described in the '369 patent, where the input current to the light emitting diodes was controlled by feedback circuitry to ensure that the output of sensor 10 fell within the range of the analog to digital converter utilized in that circuit. Such feedback control is not needed nor utilized with the instant invention greatly improving the response time and accuracy of the circuitry in processing incoming data.

In response to the energy emissions of emitters 2 and 4, photo diode 10 generates an output current which is applied to current to voltage converter 20. Current to voltage converter 20 is similar to the device described in the '369 patent and shown at 18 in FIG. 2 of the '369 patent. This device functions to convert the current output of photo diode 10 into a varying voltage level.

The output voltage of current to voltage converter 20 is applied to signal pulse extractor 45, to gate circuit 40, and to ambient light detector 80. The output signal of the current to voltage converter 20 consists of a background signal resulting from ambient light conditions and a multiplexed series of pulses corresponding to the red and infrared LED pulsed emissions. Due to the relatively small amplitude of the signal passed through blood bearing tissue, as described in the '369 patent, excessive ambient light conditions during the measurement process may result in errors. Accordingly, ambient light detector 80 monitors the output of the current to voltage converter 20 whose output is directly proportional to the amount of ambient light present during the measurement process. When the voltage output of the current to voltage converter 20 exceeds a predetermined value, as determined by ambient light detector 80, an alarm 85 is activated. It is, of course, understood that alarm 85 can be both a visual or audio alarm condition. Upon activation of the alarm 85, it would be the responsibility of the operator of the pulse oximeter to reduce ambient light in any appropriate and well known manner. The circuitry of the ambient light detector will not be described in further detail, as such circuitry would be well known to one skilled in this technical area.

A gate circuit 40 is also attached to the output of current to voltage converter 20. The purpose of gate circuit 40 is to permit the connection of the signal measuring channels to either ground or the IV converter circuit 20, under the control of CPU 100. This feature is used during an initial calibration of A/D converters 90, 95 to ensure that their outputs read zero when the input is grounded, thus eliminating any offset errors introduced by the active parts in the signal channels and the sampling circuitry which is allowed to run normally during such calibration.

The A/D converter calibration mechanism may be an integral part of the converter hardware used, and/or can be controlled by the CPU. This built in mechanism may also have its own means for calibrating full signal range such that the application of a system reference voltage to the input of the A/D converters results in the converter output reading its maximum value ($2^{20}-1$).

The foregoing zeroing of system offset can be an important part of the inventive measurement technique, as small effects can impact on measurement accuracy. It is anticipated that such compensation would be performed only once at start-up.

Figure 2A:
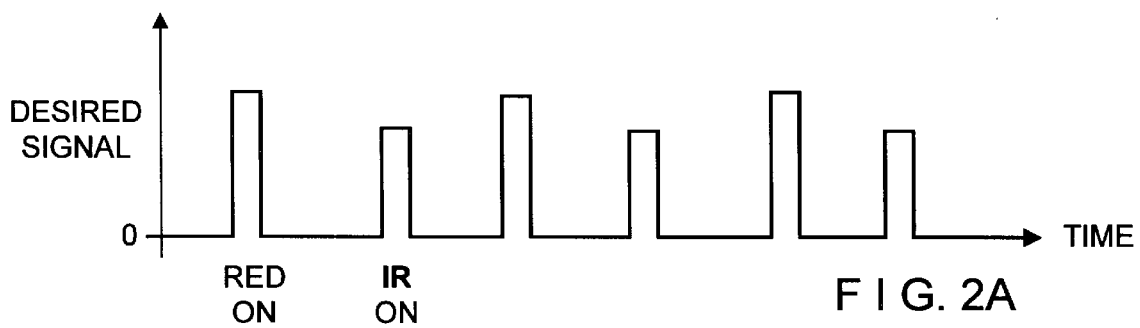
FIGS. 2A–D illustrates various waveforms analyzed in accordance with the instant invention.
Figure 2B:
Figure 2C:
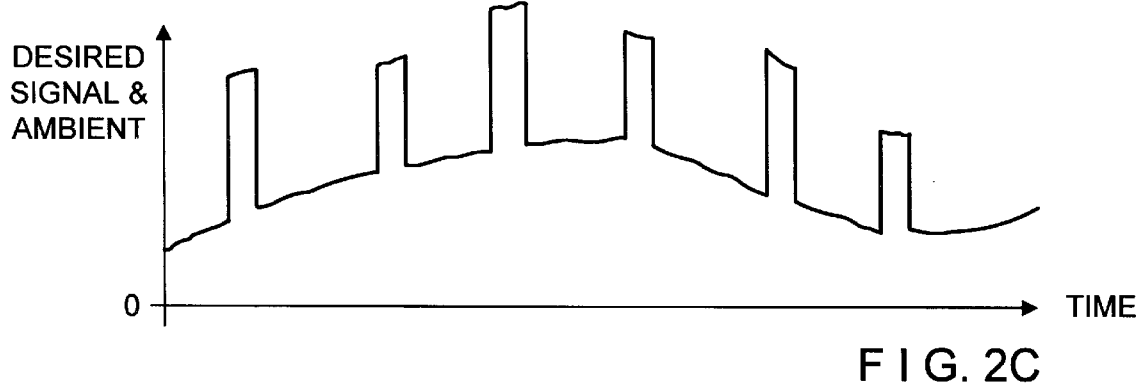
Figure 2D:
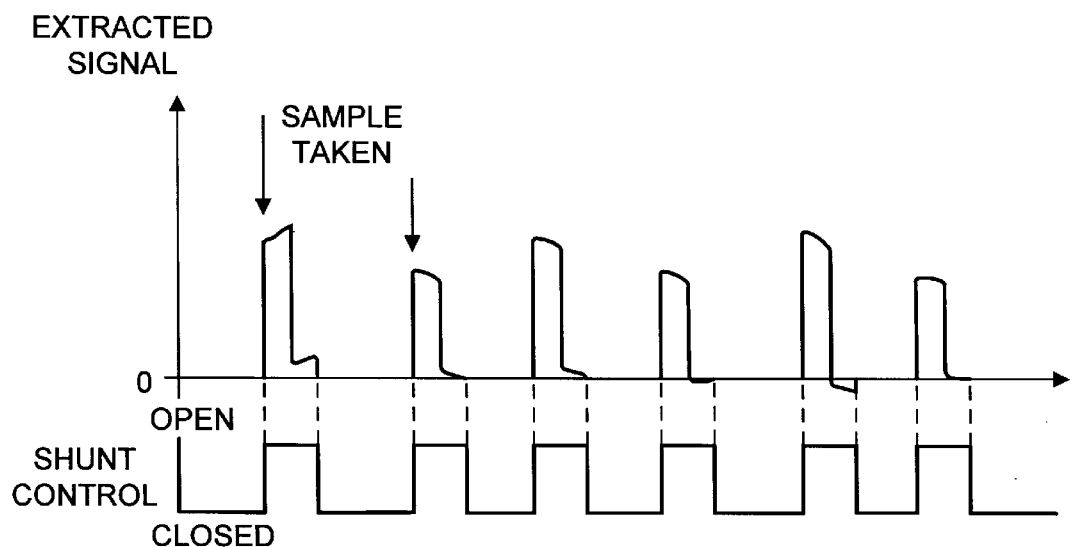

The function of signal pulse extractor 45 is to extract the incoming signal of interest from the signal generated by ambient light conditions. Recall that the desired measurement is that of the observed intensity of the two light sources in the input sensor, which desired signals are shown in FIG. 2(A). However, these signals may be combined along with other observed light, that is, ambient light as shown in FIG. 2(B). Thus, the total observed signal at the output of circuit 20 may be considered to be the sum of the desired signal and the ambient signal as shown in FIG. 2(C).

Figure 3:
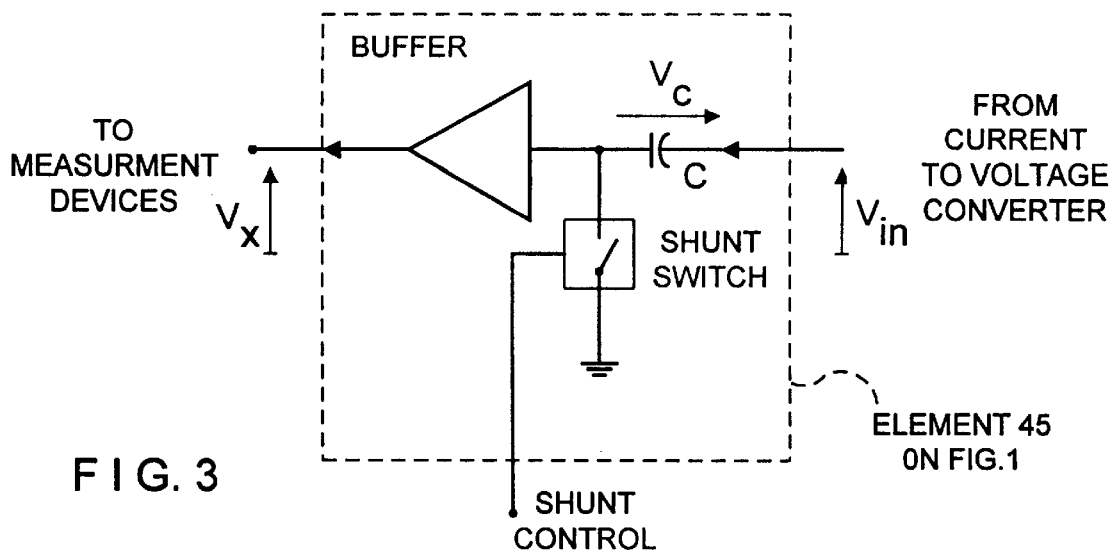
FIG. 3 is a schematic diagram of the pulse extractor utilized with the instant invention.
Figure 4A:
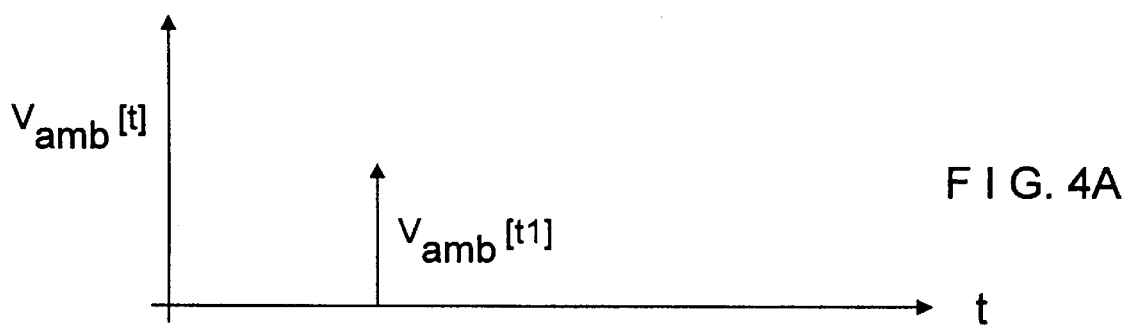
FIG. 4 illustrates various additional waveforms to be analyzed by the circuitry of the instant invention.
Figure 4B:
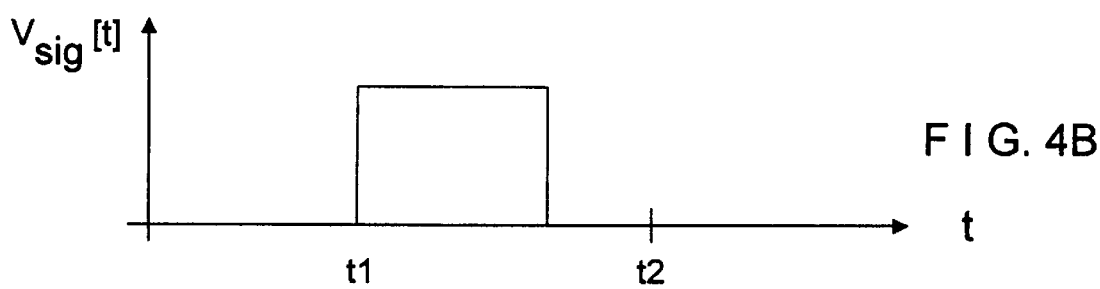
Figure 4C:
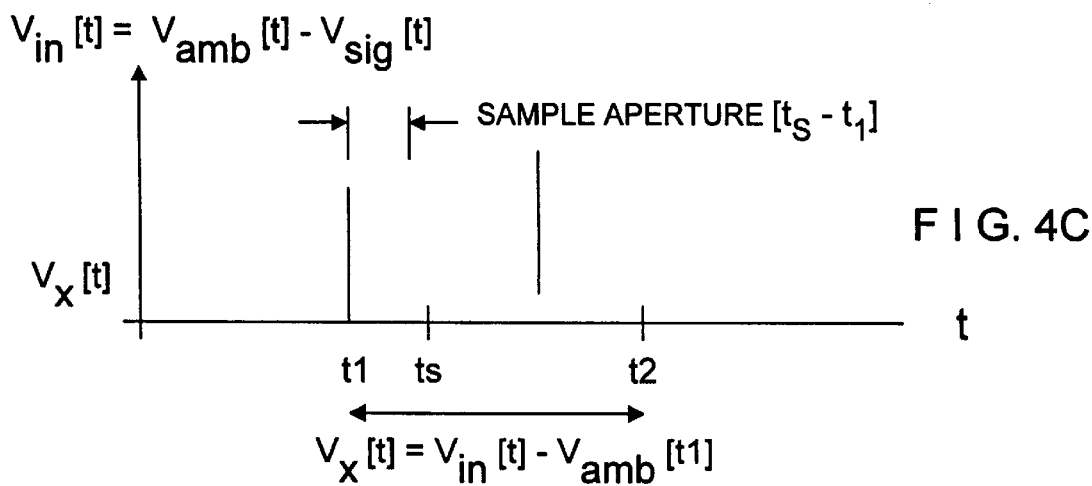

Extraction of the desired signal may be performed by a circuit of the type shown schematically in FIG. 3. The shunt switch shown in FIG. 3 may be any kind of circuit element capable of providing a low and high impedance under the control of an input signal (shunt control). When the shunt switch is closed (low impedance) the measurement output is zero (recall that all system offsets are previously calibrated out), and because of the low output impedance of the input circuit 20, the input signal voltage will appear across the capacitor C of FIG. 3. When the shunt switch is opened (high impedance), the measured output ($v_x$) consists of $V_{in}-V_c$, noting that $V_c$ will not change substantially as long as the impedances of the buffer and shunt are very high. Thus, if the shunt switch remains closed up to the time when the relevant LED source is to be pulsed on (t1), then $V_c$ will reflect $V_{in}$ due to ambient light as shown by $V_{amb}$ (t) in FIG. 4. Thus, between times t1 and t2 (shunt open) the measured signal corresponds to V(t), where:

$$V(t)=V_{in}(t)-V_{amb}(t);\ t1<t<ts=V_{sig}(t)+V_{amb}(t)-V_{amb}(t1)$$

The measurement sample is taken between t1 and ts and, thus, the error in the measurement is related to the value of $V_{amb}$ (t1) over the period t1 to ts where:

$$V_{err}\alpha V_{amb}(t)-V_{amb}(t1);\ t1<t<ts$$

Accordingly, if the sampling aperture (ts–t1) is kept as small as possible (approximately 30 microseconds is a nominal value), then errors of significant magnitude can only be introduced by $V_{amb}$ (t) signals which have high frequency components, such that the rate of change of $V_{amb}$ (t) during the short period t1–ts is significant. In practice, it has been found that ambient light signals tend to have limited bandwidth, such that a practical value for the sampling aperture may be chosen, effectively eliminating the effects of ambient light interference.

The foregoing described pulse extraction is necessary to obtain accurate measurement of observed signal intensities, and consequent $SaO_2$ values in accordance with the teachings of the instant invention. The shunt element may be controlled by timing circuit 55.

Figure 5:
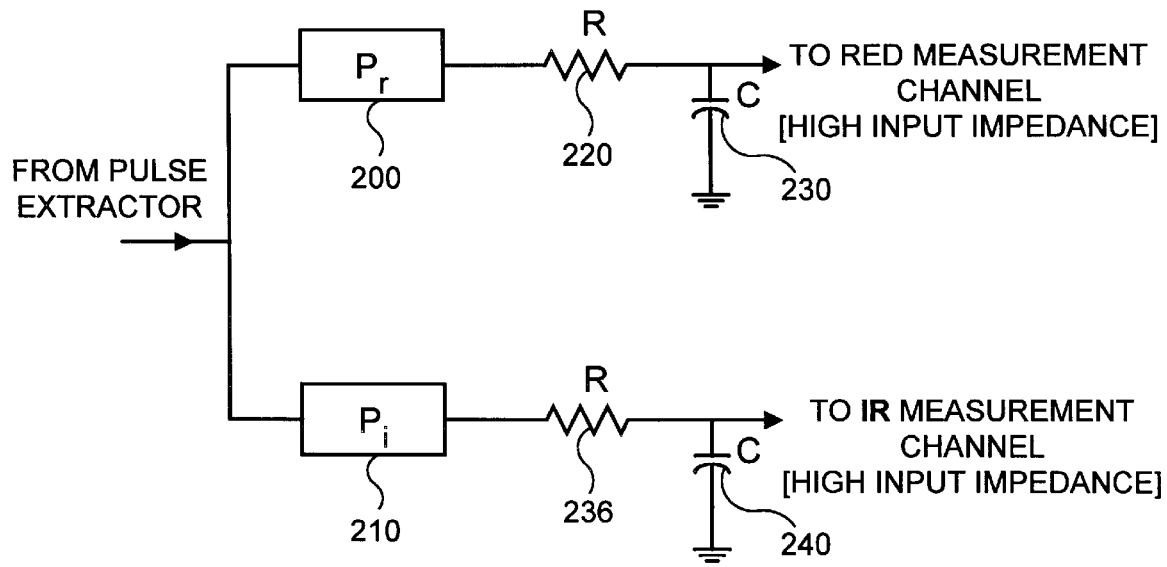
FIG. 5 is a circuit diagram illustrating one aspect of the instant invention.

The demultiplexer/sample and hold/low pass filter element 50 functions in the following manner. Under control of the timing circuit 55, two pass elements Pr and Pi (elements 200 and 210 in FIG. 5) are driven, such that Pr is activated during the sampling aperture corresponding to the red signal, and Pi similarly for the infrared signal. The resulting signals are low pass filtered by the following RC networks (elements 220–240). Note that the time constant of these networks is as follows:

$$T_{RC} \alpha \frac{t_C}{t_C - t_O}$$

where tc and to are the times for which the pass element is closed and opened respectfully.

It is to be understood that timing circuit 55 could include independent circuitry to provide appropriate timing signals or, alternatively, circuitry could, if desired, be under the control of a separate CPU or synchronized with the operation of CPU 100 as shown.

The output of circuit 50, consisting of separate red and infrared pulse trains, is amplified in a fixed gain stage consisting of fixed gain amplifiers 60 and 65. The gain of the amplifiers 60 and 65 is permanently set to optimize the signal which is subsequently applied to analog to digital converters 90 and 95. Amplifiers 60 and 65 provide only fixed gain and no means are provided in either amplifier to vary the gain in order to compensate for changes in the input signals or in other circuit conditions. The output of amplifiers 60 and 65 is in turn applied to low pass filters 70 and 75. Low pass filters 70 and 75 function essentially as noise filters in that the 20 bit analog to digital converters 90 and 95 can, under some conditions, be sensitive to noise.

The outputs of low pass filters 70 and 75 are applied to analog to digital converters 90 and 95. The use of at least a 20 bit analog to digital converter is preferred in order to achieve the advantages possible with the instant invention. More particularly, converters 90 and 95 are specifically designed to have a broad dynamic range, sufficient to accommodate the entire input signal from sensor 10 without compensation of any kind. That is, the output of sensor 10 is known to have a minimum and maximum amplitude dependent upon measurement conditions including conditions of ambient light, motion artifacts, and other aberrant input data. Utilization of analog to digital converters 90 and 95 is specifically designed knowing the minimum and maximum signal levels possible from sensor 10 and to accommodate those minimum and maximum levels.

Utilization of analog to digital converters 90 and 95 permits the ability to avoid gain compensation in order to accommodate the output of sensor 10. Also, settlement time for the circuitry is minimized providing increased response time between measurement and display.

The outputs of the analog to digital converters are directed to CPU 100 which, under control of appropriate software, and utilization of necessary memory including look up tables, etc. will analyze the output digital signals and utilize that information to calculate both oxygen saturation and/or other pertinent information. That information is then displayed at display 110. Various software systems can accomplish the necessary calculations of the oxygen saturation level described above, and one example of appropriate software is shown in the flow chart shown in FIG. 7.

Figure 7A:
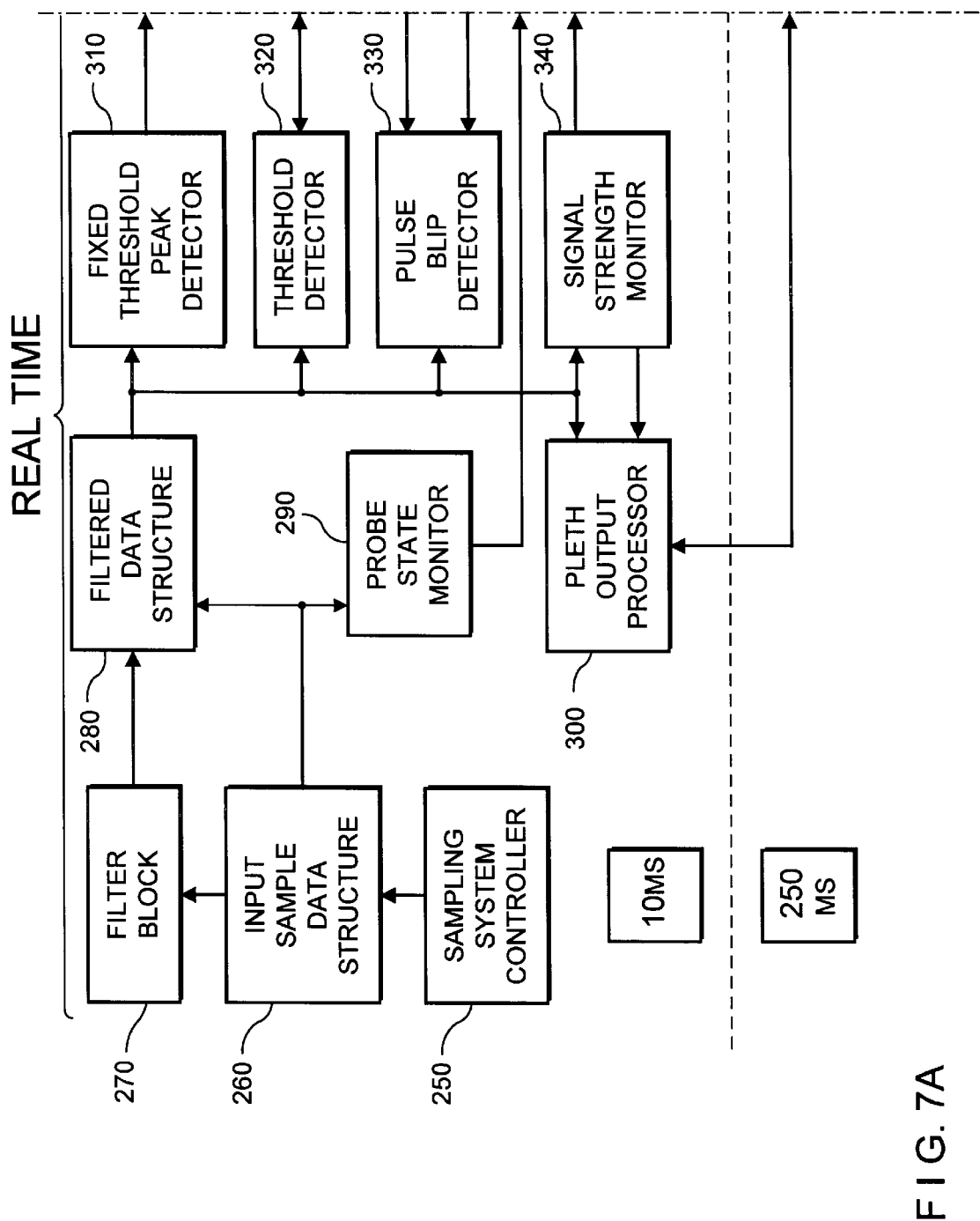
FIG. 7 is a flow chart of the software utilized in accordance with the analysis performed on incoming data.

More particularly, referring to FIG. 7, the software is divided into a "real time analysis" portion and a "background portion" as illustrated. The real time portion of the software operates with two different interrupt intervals, the first being ten microseconds, which applies to the upper dotted line portion, and a 250 microsecond interrupt interval which applies to the lower dotted line portion. The background portion of the software is utilized to analyze the data as will be described below.

Incoming data analysis begins with Sampling System Control 250. This is an interrupt driven routine which reads the output of the analog to digital converters 90 and 95 shown in FIG. 1. Routine 250 formats the incoming real time data into an Input Sample Data Structure for processing by subsequent software blocks. The Input Sample Data Structure handled by routine 260 includes the 20 bit visible red and 20 bit infrared signals extracted from the analog to digital converters, as well as an 8 bit data word which defines the state of the system hardware. For example, the 8 bit control word can be used to define the state of the system power supply, sensor status and so forth.

Incoming data, once properly formatted, is applied to Filter Block 270, which includes two digital high pass filters in a cascaded configuration. The infrared signal I(t), is applied to the cascaded filters to filter out all frequencies below 1 hertz and after, filtering is identified, for purposes of later analysis, as $P_k(t)$. At filter Block 270 the infrared signal is also differentiated (d/dt), and the differentiated signal is identified as I'(t). Similarly, the visible red signal R(t) is differentiated (d/dt) to provide R'(t). Digital data signals $P_k(t)$, I(t), I'(t), R(t) and R'(t) are then output from Filter Block 270.

The incoming data signals $P_k(t)$, I(t), I'(t), R(t), and R'(t) are next applied to Filtered Data Structure Block 280. Filtered Data Structure Block 280 stores the full 20 bit values for l(t) and R(t), which values are positive and include the DC portion of the incoming signal. Filtered Data structure block 2 stores the AC portion of the incoming signal, $P_k(t)$, I'(t), and R'(t) which signals do not have DC components. Removing the DC component allows the signals $P_k(t)$, I(t) and R(t) each to be expressed with only 16 bits, as the AC signal component of each signal is much smaller than the total AC plus DC signal component. Indeed, normally the AC signal is approximately $\frac{1}{100}$ ths of the total signal.

It is significant that the above-described separation process takes place as part of the software analysis and is not done in the hardware. Removal of the DC component from the AC component in the hardware invariably results in channel matching errors, which errors have been completely eliminated by the instant invention.

Probe State Monitor 290 utilizes the 8 bit control word previously described to determine conditions such as "probe-off" or "probe-fail" conditions. When such conditions are detected by the Probe State Monitor routine 290, an appropriate control signal is forwarded to Monitor State Controller 390, which displays the information to alert the operator of probe status.

Pleth Output Processor routine 300 operates on the $P_k(t)$ signal, to detect signal strength and produce a scaled waveform indicative of the fact that the input sensors are properly detecting a pulse from the patient being monitored. This waveform is then displayed via the Data Display Controller 430, such that the operator can view a display in the form of a bar graph, indicating that the a pulse is being properly detected.

Figure 6:
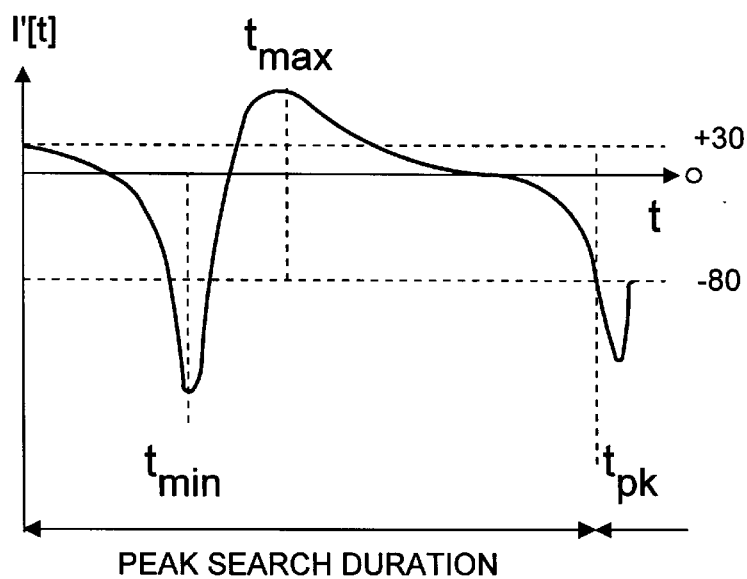
FIG. 6 is a typical waveform received during a pulse oximeter analysis.

Fixed Threshold Peak Detector 310 utilizes a conventional peak detector algorithm to detect the peaks, both positive and negative, of the incoming waveform. A typical waveform is shown in FIG. 6. The threshold levels of +30 and −80 shown in FIG. 6 are fixed thresholds based on expected values of incoming data. The software routine begins searching for a minimum $t_{min}$ when the lower threshold −80 is exceeded. A "minimum storage location" is updated periodically by the routine as the waveform continues to become more negative, with the larger negative values replacing earlier stored values. When the negative values begin to increase, the software then knows that a minimum has been reached and that minimum value, (and its time of occurrence), is then stored for later use. Similarly, when the waveform value passes the +30 level, the software begins searching for the maximum $t_{max}$ and, when located, that value, and its time of occurrence are stored. The peak search duration $t_{pk}$, is an arbitrary interval nominally chosen by the software. Once the peak search determination has been completed, the software calculates the following values:

$I_{mag}=I'(t_{max})-I'(t_{min})$
$R_{mag}=R'(t_{max})-R'(t_{min})$
$I_{mean}=[I(t_{max})+I(t_{min})]/2$
$R_{mean}=[R(t_{max})+R(t_{min})]/2$
$T_{ref}=t_{min}$
$P_{kmin}=P_k(t_{min})$ Taken together, these data values comprise the elements of each incoming data structure produced for each pulsation of blood flowing in the person being monitored.

Once the foregoing values are calculated, this block of data is then moved to the New Peak Queue Block at 350.

Threshold Detector 320 functions to check the current values of I'(t) and R'(t) to determine whether the current values lie within preset limits. For example, the threshold detector is nominally set to detect any incoming amplitude which is twice the amplitude which would be expected of a "normal" input signal. If the incoming waveform exceeds twice the amplitude of a "normal" signal, the Threshold Detector 320 alerts Data Validator 380, which is a first step in determining whether aberrant input data (such as motion artifacts) exists, as will be described below. What is considered a "normal" amplitude can be continuously monitored and changed by the software, based on past history and the Data Validator analysis which will be described.

Pulse Blip Detector 330 simply functions to detect an incoming pulse and provide an audio "beep" via Audio Processor 470. This routine is similar to the routine of 310, but performs a much less rigorous analysis as only the occurrence of a pulse is determined.

Similarly, Signal Strength Monitor 340 monitors the level of the incoming signal, and when the signal strength drops below a preset threshold, sounds an alarm via routine 390. This ensures there is sufficient signal strength for accurate calculation of oxygen saturation levels.

New Peak Queue 350 is a FIFO (first-in, first-out) buffer linking the real time portion of the software with the background signal processing loop. This avoids data loss if, for example, the background processing loop requires additional time to process prior received data while new data is arriving. Newly arrived data is placed on this que and extracted when needed for analysis.

Saturation Processor 360 is the routine that actually calculates the oxygen saturation level based on incoming data received from New Peak Queue 350. The saturation processor utilizes a well established saturation calculation algorithm to calculate the oxygen saturation level $OUT_{SAT}$ for each sampling interval (i.e. pulsation), as follows:

$$OUT_{SAT}=f\left(\frac{I_{mean}}{I_{mag}} \cdot \frac{R_{mag}}{R_{mean}}\right)$$

Three other items of data, namely $OUT_{TIME}$, $OUT_{MIN}$ and $OUT_{TAG}$ are defined as follows:
$OUT_{TIME}=T_{ref}$
$OUT_{MIN}=P_{kMin}$
$OUT_{TAG}=REJECTED$ Once calculation of the above data structure is completed, these values are placed in the Output Data Queue 400. Que Controller 370 monitors the New Peak Queue, and the Output Data Que, to control such functions as initialization and clearing the queues of data under certain conditions.

An important part of the instant invention is the fact that the software, as will be described below, checks output data prior to display to insure first that the data is valid, determines a confidence level for the data, which, if not achieved, will result in the data being ignored, and detects the occurrence of motion artifacts and other aberrant data, and will reject such data when detected. This analysis is performed by the Output Data Scanner 410, and the Data Validator 380.

Newly calculated oxygen saturation values calculated by the Saturation Processor 360 are applied to the Output Data Queue 400 prior to that data being validated. However, before that data will be used and displayed, it is necessary that it be examined and validated as "good data." The function of Output Data Scanner 410 in conjunction with Data Validator 380, is to generate a set of parameters relating to the "quality" of the newly arrived data in the Output Data Queue, and to ensure that "bad data" is not used, and to also highlight and reject motion artifacts and other aberrant data.

The Output Data Scanner examines the data in the Output Data Queue with a given set of parameters supplied by the Data Validator 380. These parameters are: (1) Clip Level; (2) Time; and (3) Threshold. Clip Level does not mean that the input signal is being "clipped" in the traditional sense. Rather, Clip Level means that the detection level is normally set at twice the level of a "normal signal" as was previously described, and when the input signal level exceeds this value, it is a possible indication that a Motion artifact, or other aberration is occurring making suspect, the newly arrived data. Time is the expected interval between beats based on historical data. That is, if the patient being monitored has a pulse rate of a certain value based on previously analyzed data, then the software expects the pulse rate to continue at approximately that same rate. If, however, there are changes in heart rate, either positive or negative, the software uses that criteria to again question the newly arrived data in the Output Data Queue. The third criteria utilized is Threshold. If the amplitude of the incoming signal becomes too small in the context of what is considered to be a normal signal, the software will again utilize that occurrence to question the newly arrived data.

All data in the Output Data Queue is tagged with one of the following categories as an indication of data quality. The categories are: (1) Rejected; (2) Dicrotic; (3) Clipped; (4) Deviant; and (5) Trashed.

The "Rejected" category means that the data is originally suspect and may, or may not, be eventually used. The "Dicrotic" category indicates that the data being analyzed may be as a result of the dicrotic notch in the blood pressure wave and not be a valid data element. The "Clipped" category means that the recently arrived data is more than twice the level of what would normally be expected as previously described. The "Deviant" category indicates that the expected pulse rate has changed and, thus, data may be suspect for that reason. The "Trashed" category is a final rejection of the data and, thereafter, that data will not be used for any purpose.

It is important, for understanding of the invention, to focus on the fact that data originally placed in a "suspect category" may eventually be used after additional validation. An example of such re-validation could occur if, for example, during the monitoring process, the patient was required to stand or move about and his heart rate increased. The newly calculated data would then be suspect and placed in the "Deviant" category. If, however, the data was then re-evaluated at a later point in time and the pulse rate, although now higher, was consistent with recent history, that data could be returned to the "normal data" category.

All data originally placed into the Output Data Queue is first tagged with a "Rejected" label. This prevents any data in the Output Data Queue from being used until that data can be validated. The validation process proceeds as two passes through the Output Data Queue.

The first pass calculates the following mean values:

$MEAN_{OK}$=Mean value of $Pk_{min}$ for all data structures where Clip Level<$Pk_{min}$<Threshold.

$MEAN_{CLIPPED}$=Mean value of $Pk_{min}$ for all data structures where $Pk_{min}$<Clip Level.

$PERIOD_{OK}$=Mean value of time intervals between consecutive data structures which qualify for $MEAN_{OK}$ and do not enclose data structures which qualify for $MEAN_{CLIPPED}$.

$PERIOD_{CLIPPED}$=Mean value of time intervals between consecutive data structures which qualify for $MEAN_{CLIPPED}$.

Figure 8:
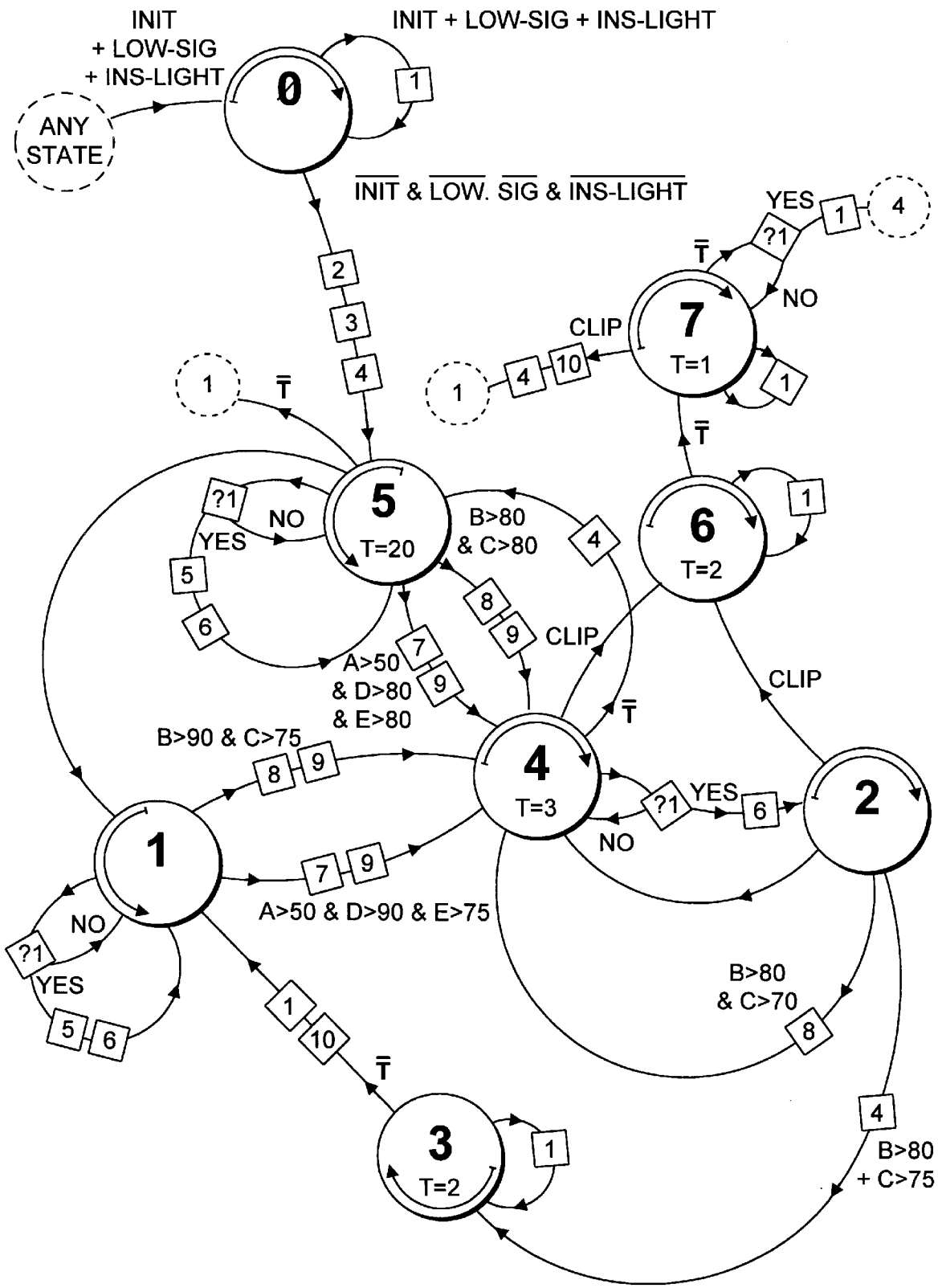
FIG. 8 is a state diagram illustrating the operation of one portion of the software.

Parameters $MEAN_{OK}$, $MEAN_{CLIPPED}$, $PERIOD_{OK}$, and $PERIOD_{CLIPPED}$ defined above, are designated in FIG. 8 and FIG. 9 as C, E, B, and D, respectively.

Tagging is performed on the first pass as follows:

All data structures qualifying for $MEAN_{OK}$ are cleared of the 'CLIPPED' or 'REJECTED' tags.

All data structures qualifying for $MEAN_{CLIPPED}$ are tagged 'CLIPPED'.

All data structures which fail to meet either are tagged 'REJECTED.'

It should also be noted that any data structure tagged as 'TRASHED' will not be used in any of the above mean calculations, and no period interval containing one or more 'TRASHED' data structures will contribute to the period means. Once set, the 'TRASHED' tag cannot be cleared. 'TRASHED' tagging is done by the Data Validator only.

The second pass tests each data structure for deviation from the relevant mean, thus, generating mean deviation for the mean values obtained from the first pass. The Output Data Scanner 410 also produces count values indicating the total number of data structures, the number of "Clipped" data structures, the number of "Rejected" data structures and the number of "Accepted" data structures.

Tagging is also performed as follows

If the period between two "Accepted" or "Clipped" data structures deviates by more than 12.5% from the relevant mean, the oldest of these data structures is tagged as "Deviant." If the deviation is less, the "Deviant" tag is cleared.

On completion of the second pass, confidence figures e.g. A, B, C, D and E as shown in FIGS. 8 and 9 are calculated for the four mean values. This confidence value is expressed as a percentage, with 100% being regarded as excellent data consistency. The figure is calculated as follows, from the mean (M), deviation (D) and number (n) of data structures upon which the mean is based, (M,D,n respectively).

$$n < 3 \quad \text{Confidence} = 100 - \frac{100D}{M}$$

$$n = 3 \quad \quad\quad\quad\quad = 88 - \frac{100D}{M}$$

$$n = 2 \quad \quad\quad\quad\quad = 75 - \frac{100D}{M}$$

If the results above give values less than zero, then they are set to zero.

Finally, the count values generated in the second pass are used to calculate the following three parameters:

Reject Percentage

Excess Amplitude Percentage

Good Percentage

Notably, the "Excess Amplitude Percentage" parameter is designated by "A" in FIGS. 8 and 9.

Based on the three calculated values and the four confidence values, i.e. A, B, C, D and E as shown in FIGS. 8 and 9, the software then decides whether the data in the Output Data Queue should, or should not, be used. Data determined to be valid is thereafter permitted to pass to the Output Data Averager 460, whose function will be described below.

Referring now to the state diagram shown in FIG. 8, the detailed operation of the Data Validator routine 380 will be described.

FIG. 8 is a state diagram illustrating the operation of the Data Validator. Starting from "any state" as illustrated, we assume that the Data Validator is being initialized in a start-up condition such that state INIT is equal to True. If state INIT is True, it causes the Data Validator to exit to state 0.

It should be noted that the arrow within each state circle indicates the sequence in which exit path conditions are tested. The description of the operation undertaken by Data Validator for each state illustrated in FIG. 8, is defined in FIG. 9.

As illustrated, as long as any of the INIT, LOW-SIG, or INS-LIGHT conditions are True, the Validator remains in state 0 and executes routine 1, indicating that all new output data is Trashed. Thus, if there is insufficient light, low signal or an initialization procedure occurring, no data will be used. Once INIT, LOW-SIG, and INS-LIGHT are all False, the second exit path from state 0 is followed and elements 2, 3 and 4 are executed on the way to state 5. Elements 2, 3 and 4, are described in FIG. 9.

Once state 5 is reached, the indication that T is equal to 20 means that this state will "time out" in 20 seconds. In particular following the priority arrow counterclockwise the "time out test" is done first. If it fails, the "clip signal" is tested (this input is signaled from the threshold detector 320 in the system block diagram FIG. 7).

If no "clipping" is signaled, the next path moves the state diagram to decision point ◇and the relevant path is then followed back to state 5. If new data is available, then the scanner parameters are set based on the new data, and a scan is performed on the output queue. The results of the scan are then tested and the relevant transitions are made.

Under normal running conditions where the sensor is on a stable patient, the state diagram will alternate between states 4 and 2. It is to be noted that paths are dependent on confidence levels A–E being less than, or greater than, certain values as illustrated in FIG. 8. As operation of the state diagram will be apparent to one skilled in the art, further description of the state paths will not be made.

Referring again to FIG. 7, Monitor State Controller 390 groups together all outputs from other sub-routines that are to be displayed. The Monitor State Controller prioritizes the information based on the predetermined urgency of a particular display, and insures that all prioritized items will take precedence over less urgent display items. For example, data indicating a probe failure would have precedence over other less critical conditions and would be displayed first. The Data Display Control 430 operates in conjunction with the Monitor State Control to resolve display conflicts.

The Keyboard Service and Menu Controller 420 provides user interface for selecting various user options. The Audio Processor 470 controls priority of the audio channel and user selected conditions, to insure appropriate audio response. Various audio options are possible which are user selected and handled by the Audio Processor. The Alert Processor 440 prioritizes alert states for presentation, while the Limit Check 450 compares the current displayed oxygen saturation and pulse rate values against user preset limits, and if a value falls outside of the preset limit an alarm is sounded. Finally, the Output Data Averager 460 averages the displayed data over a preset period of time.

It is to be understood that each of the sub-routines described in conjunction with FIG. 7 could be implemented with any appropriate software language to run on any appropriate computer. A skilled software engineer, based on the foregoing description, would readily be capable of implementing all necessary software.

The foregoing has described inter alia two major advantages of the instant invention. These advantages stem primarily from the use of an analog to digital converter to digitize the incoming signal with a dynamic range sufficient to accommodate the largest expected input signal, along with a sophisticated software package to analyze the digital signals.

The first advantage is the fact that the hardware portion of the pulse oximeter is not used in any way to separate the DC portion of the signal from the AC portion of the signal in either the infrared or visible red channels. Accordingly, all "channel matching" problems are eliminated, greatly enhancing the accuracy of the pulse oximeter.

The second advantage is the fact that the instant invention effectively detects and eliminates motion artifacts, as well as other "aberrant" data by an ingenious software analysis which continually examines the data in successive passes to ensure that data actually displayed is reliable and accurate. No other known pulse oximeters exhibit either of these advantages.

Although a specific embodiment of this invention has been shown and described, it will be understood that various modifications may be made without departing from the spirit of this invention.

We claim:

1. An apparatus for measuring and displaying oxygen saturation levels present in pulsating blood flow in a living person, comprising:

data generating means for generating incoming data structures produced by directing light having a first wavelength and light having a second wavelength, towards said pulsating blood flow, and detecting said light after passage through said pulsating blood flow;

data processing means for processing said incoming data structures so as to produce output data structures, each said output data structure including data representative of the oxygen saturation level present in one or more pulsations of said pulsating blood flow;

data storage means for storing at any instant, a plurality of output data structures produced from said data processing means;

data scanning means for scanning data in said stored output data structures, and generating for a first number of stored output data structures, a set of parameters which provide a statistical measure of confidences for said first number of stored output data structure;

data validation means for validating a second number of said output data structures on the basis of one or more of said set of parameters by operably controlling said data scanning means to mark each said output data structure in said second number thereof as being valid for use in computing oxygen saturation levels to be displayed, each said output data structure not validated by said data validation means being precluded from use in the computation of oxygen saturation levels;

computing means for computing the oxygen saturation level of said pulsating blood flow, on the basis of data contained in said second number of stored output data structures;

an output data averaging means for averaging oxygen saturation level data contained in the second number of stored output data structures; and display means for periodically displaying said computed oxygen saturation level of said pulsating blood flow.

2. The apparatus of claim 1, wherein said data generating means continuously generates one said incoming data structure for each pulsation in said pulsating blood flow, wherein said data processing means continuously produces one said output data structure for each pulsation in said pulsating blood flow; and wherein said data storage means comprises an output data storage queue, into which each said produced output data structure is continuously provided as input, temporarily stored, and periodically advanced so as to permit said output data structures from said data processing means to be temporarily stored in said output data storage queue.

3. The apparatus of claim 2, which further comprises an input data storage queue, into which said incoming data structures from said data generating means are provided as input, temporarily stored, and periodically advanced so as to provide one or more of said incoming data structures as input to said data processing means, over a predetermined time interval.

4. The apparatus of claim 3, which further comprises:

data storage queue control means for selectively controlling the advancement of said incoming data structures through said input data storage queue and the advancement of said output data structures through said output data storage queue.

5. The apparatus of claim 1, wherein said data validation means has a plurality of operational states, where during one or more of said operational states, said data scanning means is permitted to scan data in said stored output data structures and generate said set of parameters relating to a confidence level of said first number of output data structures, and where during one or more of said operational states, said data validation means is permitted to validate said second number of output data structures for use in the computation of said oxygen saturation level to be displayed.

6. The apparatus of claim 1, wherein said data scanning means further scans in a repeated manner, data in said stored output data structures and marks each said scanned output data structure as having one or more undesired data qualities, and upon each scan, reevaluates the marking of each said output data structure.

7. The apparatus of claim 6, wherein said output data averaging means selects for averaging, only output data structures within said second number of stored output data structures which are not marked as having one or more of said undesired data qualities.

8. A method of measuring and displaying average oxygen saturation levels present in pulsating blood flow in a living person, said method comprising the steps:

(a) directing light having a first wavelength and light having a second wavelength, towards a tissue sample carrying a pulsating blood flow;

(b) detecting the light of said first and second wavelengths, after passage through said tissue sample, and generating, in response thereto, a first analog electrical signal related to said first wavelength, and a second analog electrical signal related to said second wavelength;

(c) converting within a pulse oximeter said first and second analog electrical signals, into first and second digital signals, respectively;

(d) processing said first and second digital signals so as to compute, for each pulsation in said pulsating blood flow, (i) an oxygen saturation level data element, and (ii) an associated data element containing pulse time interval data or artifact data;

(e) storing said oxygen saturation level data elements and said associated data elements computed over a predetermined period of time;

(f) selectively validating certain of said oxygen saturation level data elements using said associated data elements, so as to produce validated oxygen saturation level data elements for use in computing average oxygen saturation levels for visual display;

(g) averaging a selected number of said validated oxygen saturation level data elements so as to produce data representative of an average oxygen saturation level; and (h) visually displaying from said pulse oximeter, said average oxygen saturation levels for use in monitoring said living person.

9. The method of claim 8, wherein step (e) comprises continuously providing each said oxygen saturation level data element as input into a data storage queue, temporarily storing each said oxygen saturation level therein, and periodically advancing said stored oxygen saturation levels so as to output said oxygen saturation level data elements.

10. The method of claim 9, wherein said step (f) comprises analyzing oxygen saturation level data elements stored in said data storage queue, and based on said analysis, assigning a statistical confidence measure to each analyzed oxygen saturation level data element.

11. The method of claim 10, wherein step (f) further comprises using said statistical confidence measure in order to identify and mark those analyzed oxygen saturation level data elements having one or more predefined undesired data qualities.

12. The pulse oximeter of claim 11, wherein step (f) further comprises selecting for averaging, oxygen saturation level data elements not marked as having one or more of said undesired data qualities.

13. A pulse oximeter for measuring and displaying oxygen saturation levels present in pulsating blood flow in a living person, comprising:

light direction means for directing light having a first wavelength and light having a second wavelength, towards a tissue sample carrying a pulsating blood flow;

light detection means for detecting the light of said first and second wavelengths, after passage through said tissue sample, and for generating, in response thereto, a first electrical signal related to said first wavelength, and a second electrical signal related to said second wavelength;

signal conversion means for converting said first and second electrical signals, into first and second digital signals, respectively;

computer processing means for processing said first and second digital signals so as to compute an oxygen saturation level and associated data for one or more pulsations in said pulsating flow of flood;

storage means for storing said oxygen saturation levels and associated data computed over a predetermined period of time;

data validating means for selectively validating computed oxygen saturation levels on the basis of said associated data;

averaging means for computing an average oxygen saturation level for display using a number of said computed oxygen saturation levels; and display means for visually displaying each said average oxygen saturation levels computed by said averaging means.

14. The pulse oximeter of claim 13, wherein for each said pulsation, said associated data produced from said computer processing means, comprises data selected from the group consisting of pulse time interval data and motion artifact data.

* * * * *